US012692256B2

(12) United States Patent
Graeser et al.

(10) Patent No.: US 12,692,256 B2
(45) Date of Patent: Jul. 28, 2026

(54) SALTS AND CRYSTALLINE FORMS OF A TAAR1 AGONIST

(71) Applicant: Hoffmann-La Roche Inc., Little Falls, NJ (US)

(72) Inventors: Kirsten Andrea Graeser, Basel (CH); Urs Schwitter, Reinach (CH); Frank Stowasser, Basel (CH); Florence Nicole Antoinette Tixeront, Kembs (FR); Rene Trussardi

(73) Assignee: Hoffmann-La Roche Inc., Little Falls, NJ (US)

( * ) Notice: Subject to any disclaimer, the term of this patent is extended or adjusted under 35 U.S.C. 154(b) by 784 days.

(21) Appl. No.: 17/946,743

(22) Filed: Sep. 16, 2022

(65) Prior Publication Data

US 2023/0120311 A1 Apr. 20, 2023

Related U.S. Application Data

(63) Continuation of application No. PCT/EP2021/056749, filed on Mar. 17, 2021.

(30) Foreign Application Priority Data

Mar. 19, 2020 (EP) .................................... 20164069

(51) Int. Cl.

| | |
|---|---|
| ***C07D 413/12*** | (2006.01) |
| ***A61K 31/5377*** | (2006.01) |
| ***A61P 25/00*** | (2006.01) |
| ***A61P 25/24*** | (2006.01) |

(52) U.S. Cl.

CPC ........ *C07D 413/12* (2013.01); *C07B 2200/13* (2013.01)

(58) Field of Classification Search

CPC ... C07D 413/12; C07B 2200/13; A61P 25/24; A61P 25/00; A61K 31/5377

See application file for complete search history.

(56) References Cited

U.S. PATENT DOCUMENTS 11,312,711 B2 * 4/2022 Galley ................. A61K 9/2826

FOREIGN PATENT DOCUMENTS

WO 2017/157873 A1 9/2017

OTHER PUBLICATIONS

PubChem, Ralmitaront, 2017 (Year: 2017).*

Gupta, D. et al., "Salts of Therapeutic Agents: Chemical, Physicochemical, and Biological Considerations," Molecules, 2018, vol. 23, Article 1719.

Liu, J. et al., "TAAR1 in Addiction: Looking Beyond the Tip of the Iceberg," Frontiers in Pharmacology, 2018, vol. 9, Article 279.

Harry G. Brittain, "Polymorphism in Pharmaceutical Solids," (H.G. Brittain ed., 1st ed.) 1999, pp. 1-10 and 183-226.

Augsburger and Hoag, "Pharmaceutical Dosage Forms: Tablets," (3rd Edition; vol. 2: Rational Design and Formulation) 2008, pp. 62-66.

Anderson, N., Practical Process Research and Development: A Guide for Organic Chemists "Chapter 11: Tools for Purifying the Product: Column Chromatography, Crystallization and Reslurrying" First edition, San Diego, CA-US: Academic Press—A Harcourt Science & Technology Company,:223-247 (Mar. 1, 2000).

Bastin, R., et al., "Salt Selection and Optimisation Procedures for Pharmaceutical New Chemical Entities" Org Proc Res Dev 2000 4(5):427-435 (Jul. 19, 2000).

Byrn, S., et al., "Pharmaceutical Solids: A Strategic Approach to Regulatory Considerations" Pharmaceutical Res 12(7):945-954 (Jul. 1, 1995).

"International Preliminary Report on Patentability—PCT/EP2021/056749" (Report Issuance Date; Sep. 20, 2022; Chapter I), pp. 1-10 (Sep. 29, 2022).

"International Search Report—PCT/EP2021/056749" (w/Written Opinion), pp. 1-19 (Apr. 29, 2021).

* cited by examiner

*Primary Examiner* — Bruck Kifle
*Assistant Examiner* — Kevin S Martin
(74) *Attorney, Agent, or Firm* — Morgan, Lewis & Bockius LLP

(57) ABSTRACT

Described herein are amorphous and crystalline forms of pharmaceutically acceptable salts of the TAAR1 agonist 5-ethyl-4-methyl-N-[4-[(2S) morpholin-2-yl]phenyl]-1H-pyrazole-3-carboxamide. Also described are pharmaceutical compositions suitable for administration to a mammal that include the TAAR1 agonist, and methods of using the TAAR1 agonist, alone and in combination with other compounds, for treating diseases or conditions that are associated with TAAR1 activity.

26 Claims, 2 Drawing Sheets

SALTS AND CRYSTALLINE FORMS OF A TAAR1 AGONIST

CROSS REFERENCE TO RELATED APPLICATIONS

This application is a continuation of International Application No. PCT/EP2021/056749 having an international filing date of Mar. 17, 2021, and which claims benefit of priority to European Patent Application No. 20164069.5, filed Mar. 19, 2020, all of which are incorporated herein by reference in their entirety.

FIELD OF THE INVENTION

This invention relates to novel salt forms of 5-ethyl-4-methyl-N-[4-[(2S) morpholin-2-yl]phenyl]-1H-pyrazole-3-carboxamide (hereinafter referred to as compound of Formula I), to pharmaceutical compositions comprising said salt forms, to processes for forming the salt forms and to their use in medical treatment. In addition, the present invention also relates to particular polymorphic forms of the new salt forms of the compound of Formula I described herein, as well as to pharmaceutical compositions comprising these polymorphic forms, to processes for obtaining them, and their use in medical treatment.

BACKGROUND OF THE INVENTION

WO2017157873, the entire contents of which are incorporated herein by reference, discloses the TAAR1 agonist 5-ethyl-4-methyl-N-[4-[(2S) morpholin-2-yl]phenyl]-1H-pyrazole carboxamide (Formula I), which is useful for the treatment of certain diseases and disorders of the central nervous system. The structure of 5-ethyl-4-methyl-N-[4-[(2S) morpholin-2-yl]phenyl]-1H-pyrazole-3-carboxamide (Formula I) is shown below.

(I)

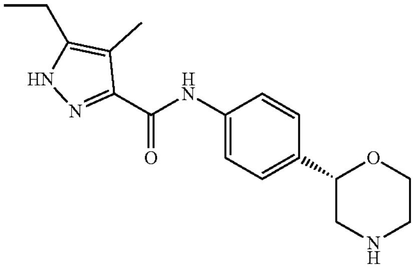

It has now surprisingly been found that certain pharmaceutically acceptable salts of the compound of Formula I, as well as certain polymorphic forms thereof, have a number of favourable properties, such as an increased shelf-life and reduced hygroscopicity, when compared to e.g. the free base disclosed in WO2017157873 or compared to other salt forms. Furthermore, a process for manufacturing the mono hydrochloride salt of the compound of Formula (I) on a large scale has been developed. The process is, inter alfa, highly reproducible, (economically) efficient and high-yielding.

SUMMARY OF THE INVENTION

In a first aspect, the present invention provides a pharmaceutically acceptable salt of 5-ethyl-4-methyl-N-[4-[(2S) morpholin-2-yl]phenyl]-1H-pyrazole-3-carboxamide (Formula I)

(I)

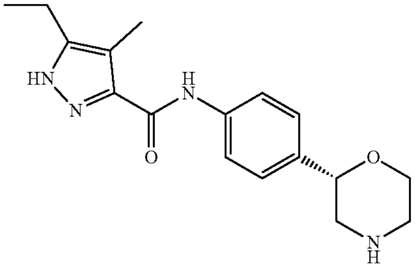

wherein the pharmaceutically acceptable salt is selected from a hydrochloric acid salt, a sulfuric acid salt, a methanesulfonic acid salt, a phosphoric acid salt, a tartaric acid salt, a fumaric acid salt, a citric acid salt, an adipic acid salt, a glycolic acid salt and a p-toluenesulfonic acid salt.

In a further aspect, the present invention provides a crystalline polymorph form A of 5-ethyl-4-methyl-N-[4-[(2S) morpholin-2-yl]phenyl]-1H-pyrazole-3-carboxamide, mono hydrochloric acid salt, wherein the crystalline form is as described herein.

In a further aspect, the present invention provides a crystalline polymorph form A of 5-ethyl-4-methyl-N-[4-[(2S) morpholin-2-yl]phenyl]-1H-pyrazole-3-carboxamide, hemi sulfuric acid salt, wherein the crystalline form is as described herein.

In a further aspect, the present invention provides a crystalline polymorph form A of 5-ethyl-4-methyl-N-[4-[(2S) morpholin-2-yl]phenyl]-1H-pyrazole-3-carboxamide, mono phosphoric acid salt, wherein the crystalline form is as described herein.

In a further aspect, the present invention provides a crystalline polymorph form A of 5-ethyl-4-methyl-N-[4-[(2S) morpholin-2-yl]phenyl]-1H-pyrazole-3-carboxamide, mono p-toluenesulfonic acid salt, wherein the crystalline form is as described herein.

In a further aspect, the present invention provides 5-ethyl-4-methyl-N-[4-[(2S) morpholin-2-yl]phenyl]-1H-pyrazole-3-carboxamide, mono hydrochloric acid salt that is in amorphous form.

In a further aspect, the present invention provides a process for manufacturing 5-ethyl-4-methyl-N-[4-[(2S) morpholin-2-yl]phenyl]-1H-pyrazole-3-carboxamide, mono hydrochloric acid salt, wherein the process is as described herein.

In a further aspect, the present invention provides a crystalline polymorph form A of 5-ethyl-4-methyl-N-[4-[(2S) morpholin-2-yl]phenyl]-1H-pyrazole-3-carboxamide, mono hydrochloric acid described herein, when obtained by the process described herein.

In a further aspect, the present invention provides a pharmaceutical composition comprising a pharmaceutically acceptable salt described herein.

In a further aspect, the present invention provides the pharmaceutically acceptable salts described herein for use as a medicament.

In a further aspect, the present invention provides the pharmaceutically acceptable salts described herein for use in the treatment of depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders (e.g. binge eating), diabetes, diabetic complications, obesity, dyslipidemia, disorders of energy consumption and assimilation, disorders and malfunction of body temperature homeostasis, disorders of sleep and circadian rhythm, cardiovascular disorders, attenuated psychotic syndrome, psychosis in neurodegenerative diseases, and apathy in neurodegenerative diseases.

DETAILED DESCRIPTION OF THE INVENTION

Figure 1:
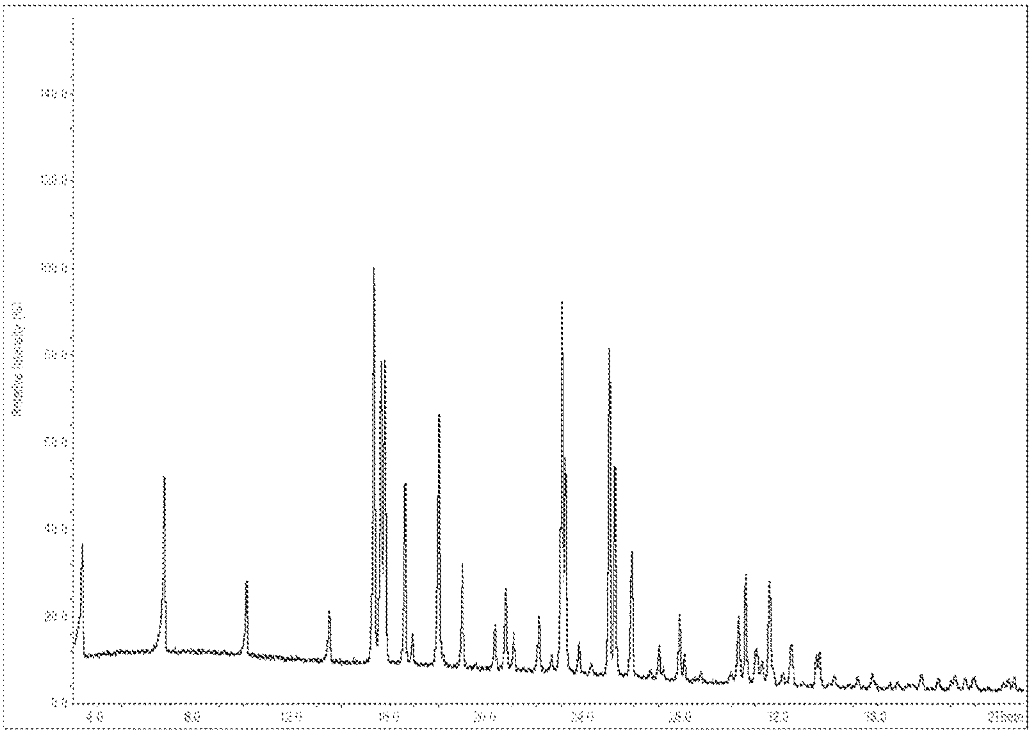
FIG. 1 illustrates the XRPD of a crystalline polymorph form A of 5-ethyl-4-methyl-N-[4-[(2S) morpholin-2-yl]phenyl]-1H-pyrazole-3-carboxamide, mono hydrochloric acid salt, with characteristic peaks at 3.4, 6.7, 10.1, 13.5, 15.4, 15.6, 15.8, 16.6, 18.0, 19.0, 20.3, 20.8, 21.1, 22.1, 23.1, 23.2 25.0, 25.2 and 25.9 [° 2 Theta±0.2° 2 Theta, Cu Kα radiation (1.5406 Å)].

5-ethyl-4-methyl-N-[4-[(2S) morpholin-2-yl]phenyl]-1H-pyrazole-3-carboxamide "5-ethyl-4-methyl-N-[4-[(2S) morpholin-2-yl]phenyl]-1H-pyrazole-3-carboxamide" refers to the compound with the following structure (Formula I):

(I)

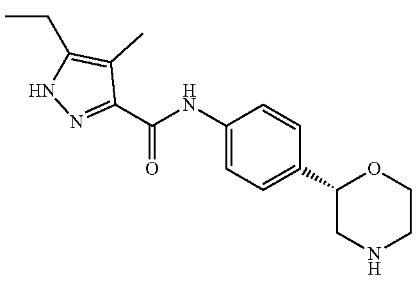

5-ethyl-4-methyl-N-[4-[(2S) morpholin-2-yl]phenyl]-1H-pyrazole-3-carboxamide is described in PCT Patent Publication No. 2017/157873.

Pharmaceutically acceptable salts of 5-ethyl-4-methyl-N-[4-[(2S) morpholin yl]phenyl]-1H-pyrazole-3-carboxamide include, but are not limited to: acid addition salts, formed by reacting the compound with a pharmaceutically acceptable inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like.

In a first aspect, the present invention provides a pharmaceutically acceptable salt of 5-ethyl-4-methyl-N-[4-[(2S) morpholin-2-yl]phenyl]-1H-pyrazole-3-carboxamide (Formula I)

(I)

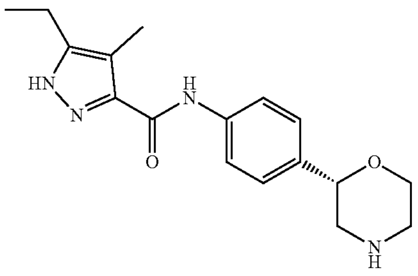

wherein the pharmaceutically acceptable salt is selected from a hydrochloric acid salt, a sulfuric acid salt, a methanesulfonic acid salt, a phosphoric acid salt, a tartaric acid salt, a fumaric acid salt, a citric acid salt, an adipic acid salt, a glycolic acid salt and a p-toluenesulfonic acid salt.

In one embodiment, the present invention provides a pharmaceutically acceptable salt of the compound of Formula (I), wherein the pharmaceutically acceptable salt is selected from a hydrochloric acid salt, a sulfuric acid salt, a phosphoric acid salt, and a p-toluenesulfonic acid salt.

In one embodiment, the present invention provides a pharmaceutically acceptable salt of the compound of Formula (I), wherein the pharmaceutically acceptable salt is the mono hydrochloric acid salt.

In one embodiment, the present invention provides a pharmaceutically acceptable salt of the compound of Formula (I), wherein the pharmaceutically acceptable salt is the hemi sulfuric acid salt.

In one embodiment, the present invention provides a pharmaceutically acceptable salt of the compound of Formula (I), wherein the pharmaceutically acceptable salt is the mono phosphoric acid salt.

In one embodiment, the present invention provides a pharmaceutically acceptable salt of the compound of Formula (I), wherein the pharmaceutically acceptable salt is the mono p-toluenesulfonic acid salt.

In one embodiment, the present invention provides a pharmaceutically acceptable salt of the compound of Formula (I) described herein, wherein the salt is in crystalline form.

5-ethyl-4-methyl-N-[4-[(2S) morpholin-2-yl]phenyl]-1H-pyrazole-3-carboxamide, mono Hydrochloric Acid Salt In one aspect, the present invention provides a crystalline polymorph form A of 5-ethyl-4-methyl-N-[4-[(2S) morpholin-2-yl]phenyl]-1H-pyrazole-3-carboxamide, mono hydrochloric acid salt that is characterized as having:

(a) an X-ray powder diffraction (XRPD) pattern with characteristic peaks at 3.4, 6.7, 10.1, 13.5, 15.4, 15.6, 15.8, 16.6, 18.0, 23.1, 23.2, 25.0, and 25.9 [° 2 Theta±0.2° 2 Theta, Cu Kα radiation (1.5406 Å)];

(b) an X-ray powder diffraction (XRPD) pattern with characteristic peaks at 3.4, 6.7, 10.1, 13.5, 15.4, 15.6, 15.8, 16.6, 18.0, 19.0, 20.3, 20.8, 21.1, 22.1, 23.1, 23.2, 25.0, 25.2 and 25.9 [° 2 Theta±0.2° 2 Theta, Cu Kα radiation (1.5406 Å)]; or (c) an X-Ray powder diffraction (XRPD) pattern substantially the same as shown in FIG. 1.

In one embodiment, said crystalline form is characterized as having property (a).

In one embodiment, said crystalline form is characterized as having property (b).

In one embodiment, said crystalline form is characterized as having property (c).

Figure 2:
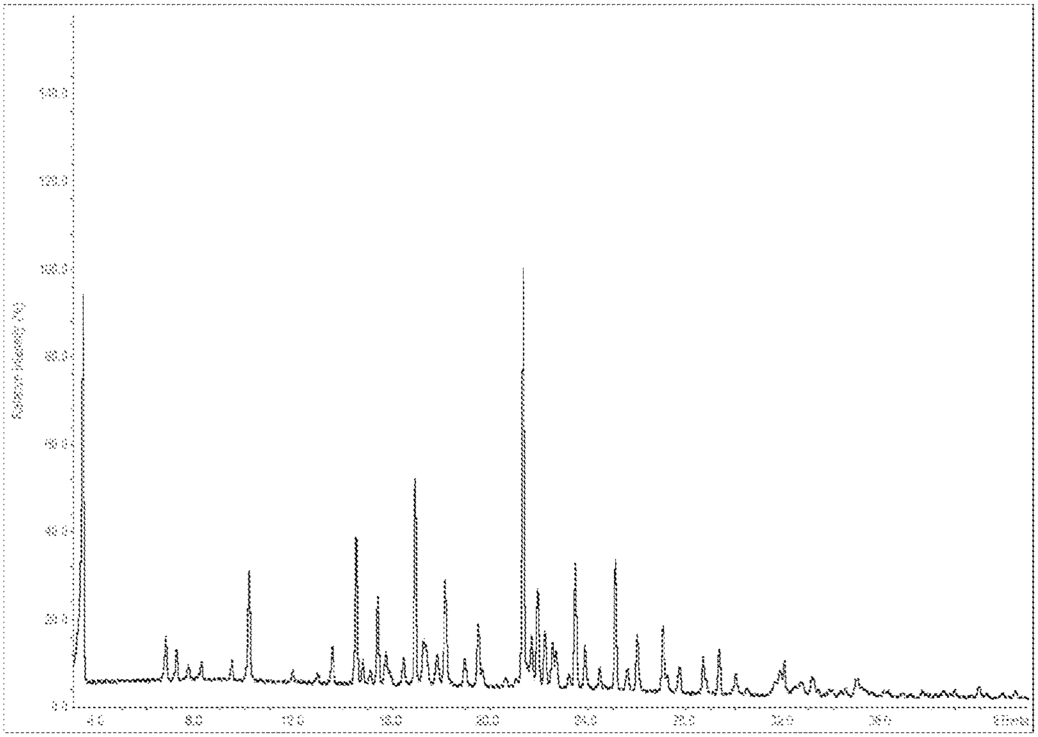
FIG. 2 illustrates the XRPD of a crystalline polymorph form A of 5-ethyl-4-methyl-N-[4-[(2S) morpholin-2-yl]phenyl]-1H-pyrazole-3-carboxamide, hemi sulfuric acid salt, with characteristic peaks at 3.4, 6.8, 10.2, 13.6, 14.5, 15.4, 16.9, 17.3, 17.4, 18.2, 19.5, 21.3, 21.7, 21.9, 22.2, 22.5, 23.5, 23.9 and 25.1 [° 2 Theta±0.2° 2 Theta, Cu Kα radiation (1.5406 Å)].

5-ethyl-4-methyl-N-[4-[(2S) morpholin-2-yl]phenyl]-1H-pyrazole-3-carboxamide, hemi sulfuric acid salt In one aspect, the present invention provides a crystalline polymorph form A of 5-ethyl-4-methyl-N-[4-[(2S) morpholin-2-yl]phenyl]-1H-pyrazole-3-carboxamide, hemi sulfuric acid salt that is characterized as having:

(a) an X-ray powder diffraction (XRPD) pattern with characteristic peaks at 3.4, 6.8, 10.2, 13.6, 14.5, 15.4, 16.9, 17.3, 17.4, 18.2, 21.3, 23.5, and 25.1 [° 2 Theta±0.2° 2 Theta, Cu Kα radiation (1.5406 Å)];

(b) an X-ray powder diffraction (XRPD) pattern with characteristic peaks at 3.4, 6.8, 10.2, 13.6, 14.5, 15.4, 16.9, 17.3, 17.4, 18.2, 19.5, 21.3, 21.7, 21.9, 22.2, 22.5, 23.5, 23.9 and 25.1 [° 2 Theta±0.2° 2 Theta, Cu Kα radiation (1.5406 Å)]; or (c) an X-Ray powder diffraction (XRPD) pattern substantially the same as shown in FIG. 2.

In one embodiment, said crystalline form is characterized as having property (a).

In one embodiment, said crystalline form is characterized as having property (b).

In one embodiment, said crystalline form is characterized as having property (c).

Figure 3:
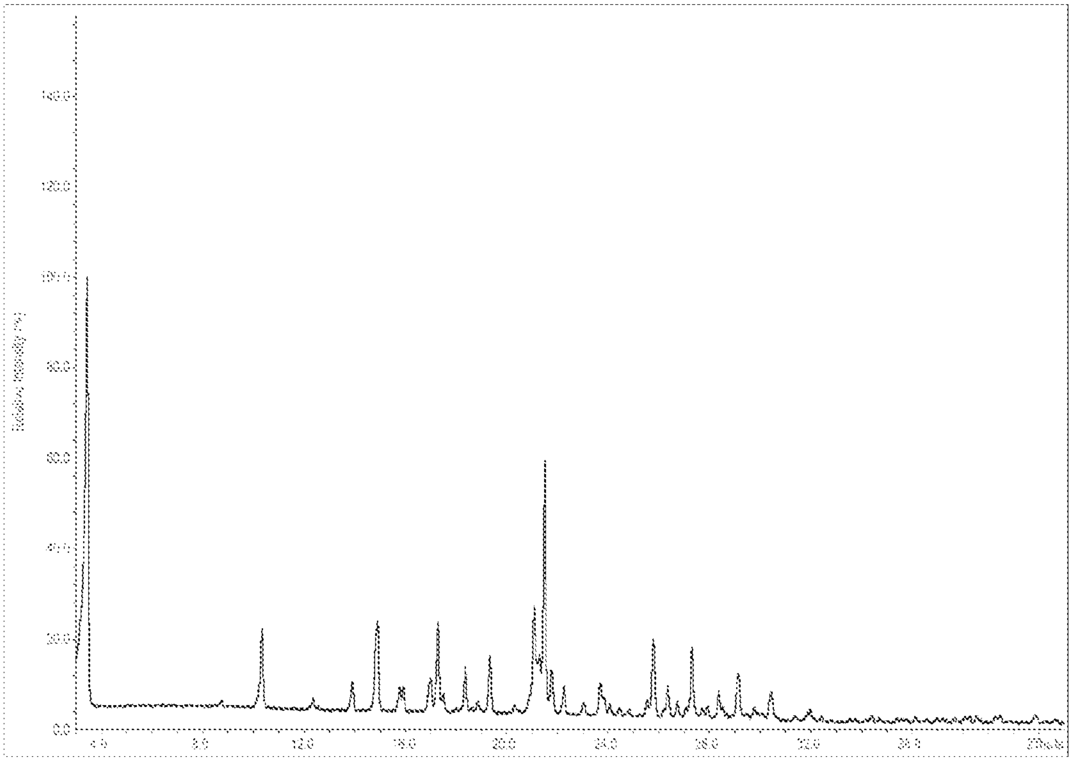
FIG. 3 illustrates the XRPD of A crystalline polymorph form A of 5-ethyl-4-methyl-N-[4-[(2S) morpholin-2-yl]phenyl]-1H-pyrazole-3-carboxamide, mono phosphoric acid salt, with characteristic peaks at 3.4, 10.3, 14.8, 14.9, 17.3, 18.4, 19.3, 21.1, 21.3, 21.5, 21.8, 25.8 and 27.3 [° 2 Theta±0.2° 2 Theta, Cu Kα radiation (1.5406 Å)].

5-ethyl-4-methyl-N-[4-[(2S) morpholin-2-yl]phenyl]-1H-pyrazole-3-carboxamide, mono phosphoric acid salt In one aspect, the present invention provides a crystalline polymorph form A of 5-ethyl-4-methyl-N-[4-[(2S) morpholin-2-yl]phenyl]-1H-pyrazole-3-carboxamide, mono phosphoric acid salt that is characterized as having:

(a) an X-ray powder diffraction (XRPD) pattern with characteristic peaks at 3.4, 10.3, 14.8, 14.9, 17.3, 18.4, 21.1, 21.5, 25.8 and 27.3 [° 2 Theta±0.2° 2 Theta, Cu Kα radiation (1.5406 Å)];

(b) an X-ray powder diffraction (XRPD) pattern with characteristic peaks at 3.4, 10.3, 14.8, 14.9, 17.3, 18.4, 19.3, 21.1, 21.3, 21.5, 21.8, 25.8 and 27.3 [° 2 Theta±0.2° 2 Theta, Cu Kα radiation (1.5406 Å)]; or (c) an X-Ray powder diffraction (XRPD) pattern substantially the same as shown in FIG. 3.

In one embodiment, said crystalline form is characterized as having property (a).

In one embodiment, said crystalline form is characterized as having property (b).

In one embodiment, said crystalline form is characterized as having property (c).

Figure 4:
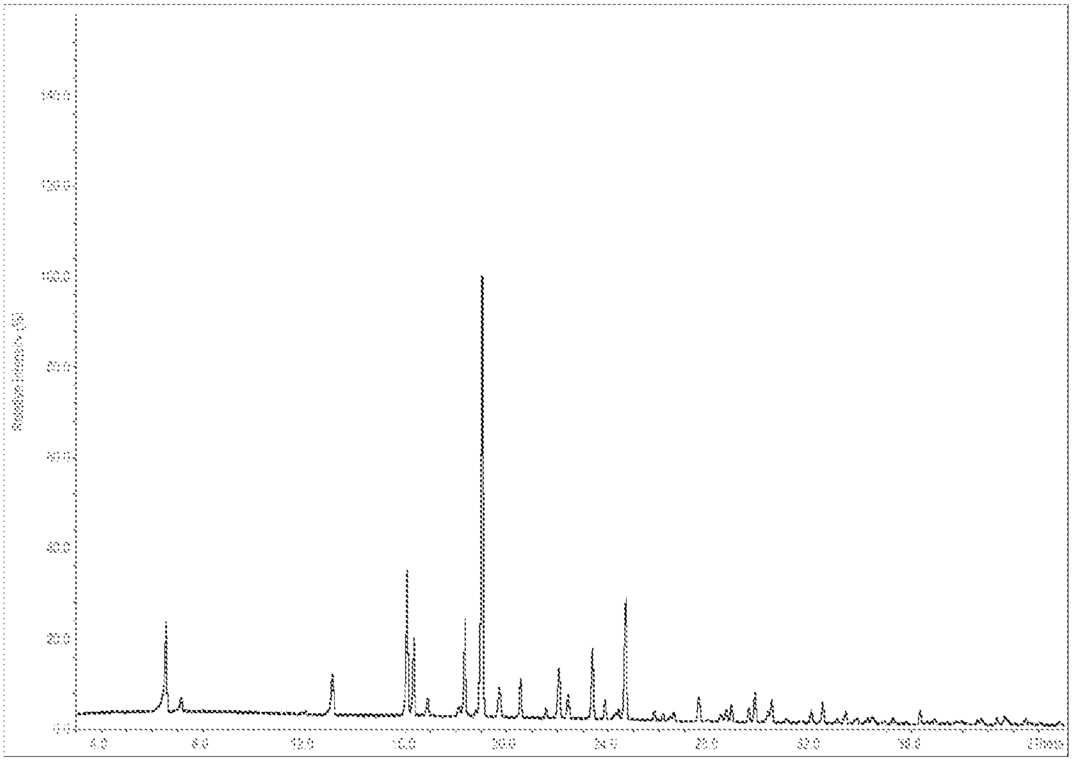
FIG. 4 illustrates the XRPD of a crystalline polymorph form A of 5-ethyl-4-methyl-N-[4-[(2S) morpholin-2-yl]phenyl]-1H-pyrazole-3-carboxamide, mono p-toluenesulfonic acid salt, with characteristic peaks at 6.6, 13.1, 16.1, 16.3, 18.3, 19.0, 19.7, 20.5, 22.1, 22.4, 23.4, 24.7 and 27.6 [° 2 Theta±0.2° 2 Theta, Cu Kα radiation (1.5406 Å)].

5-ethyl-4-methyl-N-[4-[(2S) morpholin-2-yl]phenyl]-1H-pyrazole-3-carboxamide, mono p-toluenesulfonic acid salt In one aspect, the present invention provides a crystalline polymorph form A of 5-ethyl-4-methyl-N-[4-[(2S) morpholin-2-yl]phenyl]-1H-pyrazole-3-carboxamide, mono p-toluenesulfonic acid salt that is characterized as having:

(a) an X-ray powder diffraction (XRPD) pattern with characteristic peaks at 6.6, 13.1, 16.1, 18.3, 19.0, 20.5, 23.4, and 24.7 [° 2 Theta±0.2° 2 Theta, Cu Kα radiation (1.5406 Å)];

(b) an X-ray powder diffraction (XRPD) pattern with characteristic peaks at 6.6, 13.1, 16.1, 16.3, 18.3, 19.0, 19.7, 20.5, 22.1, 22.4, 23.4, 24.7 and 27.6 [° 2 Theta±0.2° 2 Theta, Cu Kα radiation (1.5406 Å)]; or (c) an X-Ray powder diffraction (XRPD) pattern substantially the same as shown in FIG. 4.

In one embodiment, said crystalline form is characterized as having property (a).

In one embodiment, said crystalline form is characterized as having property (b).

In one embodiment, said crystalline form is characterized as having property (c).

Amorphous 5-ethyl-4-methyl-N-[4-[(2S) morpholin-2-yl]phenyl]-1H-pyrazole-3-carboxamide, mono hydrochloric acid salt In a further aspect, the present invention provides 5-ethyl-4-methyl-N-[4-[(2S) morpholin-2-yl]phenyl]-1H-pyrazole-3-carboxamide, mono hydrochloric acid salt that is in amorphous form. In some embodiments, the amorphous form of 5-ethyl-4-methyl-N-[4-[(2S) morpholin-2-yl]phenyl]-1H-pyrazole-3-carboxamide, mono hydrochloric acid salt has an XRPD pattern showing a lack of crystallinity.

Preparation of Crystalline Forms

In some embodiments, a crystalline form of a pharmaceutically acceptable salt of 5-ethyl-4-methyl-N-[4-[(2S) morpholin-2-yl]phenyl]-1H-pyrazole-3-carboxamide is prepared as outlined in the Examples. It is noted that solvents, temperatures and other reaction conditions presented herein may vary.

In one embodiment, the present invention provides a crystalline form of the mono hydrochloride salt of 5-ethyl-4-methyl-N-[4-[(2S) morpholin-2-yl]phenyl]-1H-pyrazole-3-carboxamide described herein, wherein the crystalline form is obtained using seed crystals of said crystalline form. It has been found that the present process using seed crystals is more reliable than a process whereby the resulting salt precipitates spontaneously or is brought out of a solution by adding a non-solvent. For example, it has been found that the present process using seed crystals allows control over the desired polymorphic form. Furthermore, a defined seeding procedure with respect to e.g., mass and milling grade of the seeds ensures a reproductive particle size distribution after crystallization. This is important for subsequent processing steps, such as filtration and milling.

In a further embodiment, the present invention provides a crystalline form of the mono hydrochloride salt of 5-ethyl-4-methyl-N-[4-[(2S) morpholin-2-yl]phenyl]-1H-pyrazole-3-carboxamide described herein, wherein the crystalline form is obtained from a mixture of an alcohol and water, in particular from a mixture of 1-propanol and water. It has surprisingly been found that using a mixture of water and an alcohol as opposed to an alcohol alone leads to increased solubility of 5-ethyl-4-methyl-N-[4-[(2S) morpholin-2-yl] phenyl]-1H-pyrazole-3-carboxamide, mono hydrochloride salt, allowing to run the process at higher concentrations. Running the process at higher concentrations means higher productivity because more 5-ethyl-4-methyl-N-[4-[(2S) morpholin-2-yl]phenyl]-1H-pyrazole-3-carboxamide, mono hydrochloric acid salt can be made per batch. Also, using a mixture of water and alcohol instead of just an alcohol has the advantage that an aqueous solution of HCl can be employed instead of highly volatile and reactive acetyl chloride. That is, the process of the present invention reduces the use of hazardous chemicals. In addition, due to a higher solubility of 5-ethyl-4-methyl-N-[4-[(2S) morpholin-2-yl]phenyl]-1H-pyrazole-3-carboxamide, mono hydrochloride salt at identical temperatures by increasing the water content, the final polish filtration, which is good practice on the final step in a GMP environment, can be performed at lower temperatures. This improves the technical feasibility of the polish filtration, as some polish filters have temperature limitations because of physical stability or pose a risk with respect to extractables at higher temperatures.

In summary, the process of the present invention is well suited for industrial scale production of 5-ethyl-4-methyl-N-[4-[(2S) morpholin-2-yl]phenyl]-1H-pyrazole-3-carboxamide, mono hydrochloric acid salt.

In one aspect, the present invention provides a process for manufacturing 5-ethyl-4-methyl-N-[4-[(2S) morpholin-2-yl]phenyl]-1H-pyrazole-3-carboxamide, mono hydrochloric acid salt comprising:

(a) reacting 5-ethyl-4-methyl-N-[4-[(2S) morpholin-2-yl] phenyl]-1H-pyrazole-3-carboxamide with hydrochloric acid; and (b) adding seed crystals of 5-ethyl-4-methyl-N-[4-[(2S) morpholin-2-yl]phenyl]-1H-pyrazole-3-carboxamide, mono hydrochloric acid salt to the mixture obtained from step a).

In one embodiment, steps (a) and (b) of the process of the invention are performed in a solvent mixture of an alcohol and water. The benefits of using such a mixture as opposed to an alcohol alone have been outlined above. In one embodiment, the alcohol solvent used in steps (a) and (b) of the process of the invention is 1-propanol. In one embodiment, the ratio of alcohol to water in the solvent mixture used in step (a) of the process of the invention is about 15:1 vol/vol.

In one embodiment, the hydrochloric acid in step (a) of the process of the invention is added as an aqueous solution. In one embodiment, said aqueous solution of hydrochloric acid comprises about 25% wt/wt of hydrochloric acid.

In one embodiment, the process of the invention further comprises step (c): reducing the water content of the reaction mixture by distillation. It has surprisingly been found that this process step increases the final yield of 5-ethyl-4-methyl-N-[4-[(2S) morpholin-2-yl]phenyl]-1H-pyrazole carboxamide, mono hydrochloric acid. In one embodiment, the water content after said reducing the water content of the reaction mixture is about 2% wt/wt. In one embodiment, the volume of the reaction mixture during said reducing the water content of the reaction mixture is kept constant by continuous addition of an organic solvent, in particular an alcohol, most preferably 1-propanol.

In one embodiment, the process of the invention further comprises step (d): cooling. In one embodiment, said cooling is cooling to 0° C.+/−5 C In one embodiment, the process of the invention further comprises step (e): ageing. In one embodiment, said ageing is ageing at 0° C.+/−5 C. In one embodiment, said ageing is ageing for at least 4 h.

In one embodiment, said seed crystals in step (b) of the process of the invention are added as a suspension in an organic solvent. In one embodiment, said organic solvent is 1-propanol.

In one aspect, the present invention provides a crystalline polymorph form A of 5-ethyl-4-methyl-N-[4-[(2S) morpholin-2-yl]phenyl]-1H-pyrazole-3-carboxamide, mono hydrochloric acid described herein, when obtained by the process of the invention described herein.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

In some embodiments, compositions comprising a crystalline form of a pharmaceutically acceptable salt of 5-ethyl-4-methyl-N-[4-[(2S) morpholin-2-yl]phenyl]-1H-pyrazole-3-carboxamide (e.g. 5-ethyl-4-methyl-N-[4-[(2S)

morpholin-2-yl]phenyl]-1H-pyrazole-3-carboxamide, mono hydrochloric acid salt) include a residual amount of an organic solvent(s). In some embodiments, compositions comprising a crystalline form of a pharmaceutically acceptable salt of 5-ethyl-4-methyl-N-[4-[(2S) morpholin-2-yl] phenyl]-1H-pyrazole-3-carboxamide (e.g. 5-ethyl-4-methyl-N-[4-[(2S) morpholin-2-yl]phenyl]-1H-pyrazole-3-carboxamide, mono hydrochloric acid salt) include a detectable amount of an organic solvent(s). In some embodiments, compositions comprising a crystalline form of a pharmaceutically acceptable salt of 5-ethyl-4-methyl-N-[4-[(2S) morpholin-2-yl]phenyl]-1H-pyrazole-3-carboxamide (e.g. 5-ethyl-4-methyl-N-[4-[(2S) morpholin-2-yl]phenyl]-1H-pyrazole-3-carboxamide, mono hydrochloric acid salt) include a residual amount of a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from the group consisting of 1-butanol, 2-butanol, ethanol, 3-methyl-1-butanol, 2-methyl-1-propanol, 1-pentanol, 1-propanol, and 2-propanol. In some embodiments, the Class 3 solvent is 1-propanol.

The methods and compositions described herein include the use of a crystalline form of a pharmaceutically acceptable salt of 5-ethyl-4-methyl-N-[4-[(2S) morpholin-2-yl] phenyl]-1H-pyrazole-3-carboxamide (e.g. 5-ethyl-4-methyl-N-[4-[(2S) morpholin-2-yl]phenyl]-1H-pyrazole-3-carboxamide, mono hydrochloric acid salt). In addition, the crystalline forms of the pharmaceutically acceptable salt of 5-ethyl-4-methyl-N-[4-[(2S) morpholin-2-yl]phenyl]-1H-pyrazole-3-carboxamide (e.g. 5-ethyl-4-methyl-N-[4-[(2S) morpholin-2-yl]phenyl]-1H-pyrazole-3-carboxamide, mono hydrochloric acid salt) described herein can exist in unsolvated as well as solvated forms with pharmaceutically acceptable solvents such as water, 1-propanol, ethanol, and the like.

Certain Terminology

The term "pharmaceutical composition" refers to a mixture of a crystalline form of a pharmaceutically acceptable salt of 5-ethyl-4-methyl-N-[4-[(2S) morpholin-2-yl]phenyl]-1H-pyrazole-3-carboxamide (e.g. 5-ethyl-4-methyl-N-[4-[(2S) morpholin-2-yl]phenyl]-1H-pyrazole-3-carboxamide, mono hydrochloric acid salt), with other chemical components, such as carriers, stabilizers, diluents, dispersing agents, suspending agents, thickening agents, excipients, etc. The pharmaceutical composition facilitates administration of the compound to a mammal.

Administration of a combination of agents, as used herein, includes administration of the agents described in a single composition or in a combination therapy wherein one or more agent is administered separately from at least one other agent.

"Detectable amount" refers to an amount that is measurable using standard analytic methods (e.g. ion chromatography, mass spectrometry, NMR, HPLC, gas chromatography, elemental analysis, IR spectroscopy, inductively coupled plasma atomic emission spectrometry, USP<231>Method II, etc) (ICH guidances, Q2A Text on Validation of Analytical Procedures (March 1995) and Q2B Validation of Analytical Procedures: Methodology (November 1996)).

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. The term "therapeutically effective amount" includes, for example, a prophylactically effective amount. The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study. In some embodiments, the term "effective amount" or "therapeutically effective amount," is used in reference to 5-ethyl-4-methyl-N-[4-[(2S) morpholin-2-yl] phenyl]-1H-pyrazole-3-carboxamide, or a pharmaceutically acceptable salt thereof, and refers to a sufficient amount of 5-ethyl-4-methyl-N-[4-[(2S) morpholin-2-yl]phenyl]-1H-pyrazole-3-carboxamide, or a pharmaceutically acceptable salt thereof, being administered which will relieve to some extent one or more of the symptoms of the disease or condition being treated.

The terms "kit" and "article of manufacture" are used as synonyms.

Pharmaceutical Compositions/Formulations

Pharmaceutical compositions are formulated in a conventional manner using one or more physiologically acceptable carriers comprising excipients and auxiliaries which facilitate processing of the active compounds into preparations which are used pharmaceutically. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins1999), herein incorporated by reference in their entirety.

In one aspect, the present invention relates to a pharmaceutical composition comprising a pharmaceutically acceptable of salt 5-ethyl-4-methyl-N-[4-[(2S) morpholin-2-yl] phenyl]-1H-pyrazole-3-carboxamide described herein (e.g. 5-ethyl-4-methyl-N-[4-[(2S) morpholin-2-yl]phenyl]-1H-pyrazole-3-carboxamide, mono hydrochloric acid salt) and at least one additional ingredient selected from pharmaceutically acceptable carriers, diluents and excipients.

In some embodiments, the present invention relates to a pharmaceutical composition comprising a crystalline form of a pharmaceutically acceptable of salt 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H- pyrazole-3-carboxamide, mono hydrochloric acid salt) and at least one additional ingredient selected from pharmaceutically acceptable carriers, diluents and excipients.

In some embodiments, a crystalline form of a pharmaceutically acceptable salt of 5-ethyl-4-methyl-N-[4-[(2S) morpholin-2-yl]phenyl]-1H-pyrazole-3-carboxamide described herein (e.g. 5-ethyl-4-methyl-N-[4-[(2S) morpholin-2-yl]phenyl]-1H-pyrazole-3-carboxamide, mono hydrochloric acid salt), is formulated for oral administration to a mammal. In some embodiments, a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), is formulated into an oral dosage form. In some embodiments, a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), is formulated into a solid oral dosage form. In some embodiments, a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), is formulated into a tablet, coated tablet, dragée, hard gelatin capsule, soft gelatin capsule, powder, solution, suspension, emulsion, and the like, for oral ingestion by a mammal.

Contemplated pharmaceutical compositions provide a therapeutically effective amount of a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), enabling, for example, once-a-day, twice-a-day, three times a day, etc. administration. In one embodiment, pharmaceutical compositions provide an effective amount of a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), enabling once-a-day dosing.

Dose Amounts

In certain embodiments, the amount of a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), in the pharmaceutical compositions is about 0.5 mg to about 1000 mg per dose, preferably about 0.5 mg to about 100 mg per dose, more preferably about 0.5 mg to about 20 mg per dose.

In a preferred embodiment, the amount of a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin yl]phenyl]-1H-pyrazole-3-carboxamide, mono hydrochloric acid salt), in the pharmaceutical compositions is about 20 mg to about 400 mg per dose, prefereably about 30 mg to about 350 mg per dose, more preferably about 45 mg to about 300 mg per dose.

In certain embodiments, the amount of a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), in the pharmaceutical compositions is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg or about 20 mg.

In one embodiment, the desired dose is conveniently presented in a single dose or in divided doses administered simultaneously (or over a short period of time) or at appropriate intervals, for example as two, three, four or more sub-doses per day.

In one embodiment, the daily dosages appropriate for a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), is from about 0.01 to about 30 mg, in particular from about 10 to about 20 mg, most particularly 18 mg. In other embodiments, the daily dosage or the amount of active in the dosage form are lower or higher than the ranges indicated herein.

Methods of Treatment, Methods of Dosing and Treatment Regimens

In one aspect, the present invention provides a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt) for use as a medicament.

In a further aspect, the present invention provides a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt) for use in the treatment of depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders (e.g. binge eating), diabetes, diabetic complications, obesity, dyslipidemia, disorders of energy consumption and assimilation, disorders and malfunction of body temperature homeostasis, disorders of sleep and circadian rhythm, cardiovascular disorders, attenuated psychotic syndrome, psychosis in neurodegenerative diseases, and apathy in neurodegenerative diseases in a mammal.

In a further aspect, the present invention provides a pharmaceutical composition described herein for use in the treatment of depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders (e.g. binge eating), diabetes, diabetic complications, obesity, dyslipidemia, disorders of energy consumption and assimilation, disorders and malfunction of body temperature homeostasis, disorders of sleep and circadian rhythm, cardiovascular disorders, attenuated psychotic syndrome, psychosis in neurodegenerative diseases, and apathy in neurodegenerative diseases in a mammal.

In a further aspect, the present invention provides a method of treating depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders (e.g. binge eating), diabetes, diabetic complications, obesity, dyslipidemia, disorders of energy consumption and assimilation, disorders and malfunction of body temperature homeostasis, disorders of sleep and circadian rhythm, cardiovascular disorders, attenuated psychotic syndrome, psychosis in neurodegenerative diseases, and apathy in neurodegenerative diseases in a mammal comprising administering a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt) to the mammal in need thereof.

In a further aspect, the present invention provides a method of treating depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders (e.g. binge eating), diabetes, diabetic complications, obesity, dyslipidemia, disorders of energy consumption and assimilation, disorders and malfunction of body temperature homeostasis, disorders of sleep and circadian rhythm, cardiovascular disorders, attenuated psychotic syndrome, psychosis in neurodegenerative diseases, and apathy in neurodegenerative diseases in a mammal comprising administering a pharmaceutical composition described herein to the mammal in need thereof.

In a further aspect, the present invention provides the use of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt) in a method of manufacturing a medicament for the treatment of depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders (e.g. binge eating), diabetes, diabetic complications, obesity, dyslipidemia, disorders of energy consumption and assimilation, disorders and malfunction of body temperature homeostasis, disorders of sleep and circadian rhythm, cardiovascular disorders, attenuated psychotic syndrome, psychosis in neurodegenerative diseases, and apathy in neurodegenerative diseases in a mammal.

In a further aspect, the present invention provides the use of a pharmaceutical composition described herein in a method of manufacturing a medicament for the treatment of depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders (e.g. binge eating), diabetes, diabetic complications, obesity, dyslipidemia, disorders of energy consumption and assimilation, disorders and malfunction of body temperature homeostasis, disorders of sleep and circadian rhythm, cardiovascular disorders, attenuated psychotic syndrome, psychosis in neurodegenerative diseases, and apathy in neurodegenerative diseases in a mammal.

In a further aspect, the present invention provides the use of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin yl]phenyl]-1H-pyrazole-3-carboxamide, mono hydrochloric acid salt) in a method of treating described herein.

In a further aspect, the present invention provides the use of a pharmaceutical composition described herein in a method of treating described herein.

Diseases or conditions that may be treated using a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt) include all diseases that are associated with TAAR1 activity. In a particular embodiment, the pharmaceutically acceptable salts and pharmaceutical compositions described herein are useful for treating diseases or conditions selected from bipolar disorder, schizophrenia, substance abuse, addiction, eating disorders (e.g. binge eating), diabetes, attenuated psychotic syndrome, psychosis in neurodegenerative diseases, and apathy in neurodegenerative diseases. In a preferred embodiment, the pharmaceutically acceptable salts and pharmaceutical compositions described herein are useful for treating schizophrenia. In a further preferred embodiment, the pharmaceutically acceptable salts and pharmaceutical compositions described herein are useful for treating schizophrenia and manic episodes associated with bipolar disorders with reduced incidence of metabolic syndrome. In a further preferred embodiment, the pharmaceutically acceptable salts and pharmaceutical compositions described herein are useful for treating schizophrenia and manic episodes associated with bipolar disorders with antidiabetic efficacy. In a further preferred embodiment, the pharmaceutically acceptable salts and pharmaceutical compositions described herein are useful for treating schizophrenia and manic episodes associated with bipolar disorders with antidiabetic efficacy, which results in lowering blood glucose excursion. In a further preferred embodiment, the pharmaceutically acceptable salts and pharmaceutical compositions described herein are useful for treating schizophrenia and manic episodes associated with bipolar disorders with antidiabetic efficacy, which results in lowering fat mass and body weight.

In one embodiment, the pharmaceutical compositions described herein comprising a crystalline form of a pharmaceutically acceptable salt of 5-ethyl-4-methyl-N-[4-[(2S) morpholin yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt) are administered for prophylactic and/or therapeutic treatments. In therapeutic applications, the compositions are administered to a patient already suffering from a disease or condition, in an amount sufficient to cure or at least partially arrest at least one of the symptoms of the disease or condition. In certain embodiments, amounts effective for this use depend on the severity and course of the disease or condition, previous therapy, the patient's health status, weight, and response to the drugs, and/or the judgment of the treating physician.

In prophylactic applications, the pharmaceutical compositions described herein comprising a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt) are administered to a patient susceptible to or otherwise at risk of a particular disease, disorder or condition. Such an amount is defined to be a "prophylactically effective amount or dose." In this use, the precise amounts also depends on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments, administration of the compound, compositions or therapies as described herein includes chronic administration. In certain embodiments, chronic administration includes administration for an extended period of time, including, e.g., throughout the duration of the patient's life in order to ameliorate or otherwise control or limit the symptoms of the patient's disease or condition. In some embodiments, chronic administration includes daily administration.

In some embodiments, administration of the compound, compositions or therapies described herein is given continuously. In alternative embodiments, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

Combination Treatments

In certain instances, it is appropriate to administer a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), in combination with another therapeutic agent. In one embodiment, the other therapeutic agent is an antipsychotic. In one embodiment, the other therapeutic agent is an atypical antipsychotic. In one embodiment, the other therapeutic agent is an antipsychotic selected from the group consisting of olanzapine (Zyprexa®), clozapine (Clorazil®), risperidone (Risperdal®), aripiprazole (Abilify®) and ziprasidone (Geodon®). In a preferred embodiment, the other therapeutic agent is olanzapine (Zyprexa®).

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

In various embodiments, a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), is administered concurrently (e.g., simultaneously, essentially simultaneously or within the same treatment protocol) or sequentially, depending upon the nature of the disease and the condition of the patient. In certain embodiments, the determination of the order of administration, and the number of repetitions of administration of each therapeutic agent during a treatment protocol, is based upon evaluation of the disease being treated and the condition of the patient.

For combination therapies described herein, dosages of the co-administered compounds vary depending on the type of co-drug employed, on the specific drug employed, on the disease or condition being treated and so forth.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent (s) or carrier(s).

Kits/Articles of Manufacture

For use in the therapeutic methods of use described herein, kits/articles of manufacture are also described herein. Such kits include a carrier, package, or container that is optionally compartmentalized to receive one or more doses of a pharmaceutical composition of a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl methyl-N-[4-[(2S) morpholin-2-yl]phenyl]-1H-pyrazole-3-carboxamide, mono hydrochloric acid salt), for use in a method described herein. The kits provided herein contain packaging materials. Packaging materials for use in packaging pharmaceutical products include, but are not limited to those described in e.g., U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment. A wide array of formulations of a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), and compositions thereof are contemplated as are a variety of treatments for any disease, disorder, or condition that would benefit by treatment with an TAAR1 agonist.

For example, the container(s) include a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a crystalline form of a pharmaceutically acceptable salt of 5-ethyl-4-methyl-N-[4-[(2S) morpholin-2-yl]phenyl]-1H-pyrazole-3-carboxamide described herein (e.g. a crystalline polymorph form A of 5-ethyl-4-methyl-N-[4-[(2S) morpholin-2-yl]phenyl]-1H-pyrazole-3-carboxamide, mono hydrochloric acid salt), formulated in a compatible pharmaceutical carrier are also prepared, placed in an appropriate container, and labeled for treatment of an indicated condition.

EXAMPLES

Example 1: Salt Forms of 5-ethyl-4-methyl-N-[4-[(2S) morpholin-2-yl]phenyl]-1H-pyrazole-3-carboxamide For each salt formation experiment 5-ethyl-4-methyl-N-[4-[(2S) morpholin-2-yl]phenyl]-1H-pyrazole-3-carboxamide (approx. 450 mg) was dissolved in dioxane (approx. 90 mL) at elevated temperature (approx. 90° C.) in a 100 mL glass vial. The clear solution was then cooled to 60° C. (to approx. 40° C. for adipic acid) prior to the addition of approx. 1.1 equivalents (approx. 0.55 equivalents for sulfuric acid) of a 0.5 M (0.2 M for fumaric acid) stock solution in dioxane of the respective acid under agitation. The reaction mixture was then allowed to reach ambient temperature passively and further agitated overnight. In the cases of adipic acid, the solvent was partially evaporated at this stage to increase the yield. The solid residue was collected by filtration and rinsed with approx. 2 mL of dioxane. A sample of the wet product was analyzed by XRPD. The remainder of the product was dried in a vacuum tray dryer at 50° C./<10 mbar for 2 days prior to analysis by XRPD, DSC, TGA, and, if appropriate, also by DVS.

TABLE 1

Crystallinities, Melting Temperatures, and Hygroscopicities of Crude Salt Forms of 5-ethyl-4-methyl-N-[4-[(2S)morpholin-2-yl]phenyl]-1H-pyrazole-3-carboxamide

| Salt former[1)] | Crystal-linity | Melting temperature ($T_{onset}$ DSC) | Hygroscopicity[2)] |
|---|---|---|---|
| Hydrochloric acid | high | melting under decomposition at >270° C. | Slightly hygroscopic (0.5%-m/m weight increase) |
| Sulfuric acid | moderate | melting under decomposition at >200° C. | Not analyzed |
| Methanesulfonic acid | high | 217° C. | Hygroscopic (8.5%-m/m weight increase) (phase transformation at >80%-RH at 25° C.) |
| Phosphoric acid | high | Melting under decomposition at >220° C. | Slightly hygroscopic |
| L(+)-Tartaric acid | high | melting under decomposition at >210° C. | Slightly hygroscopic |
| Fumaric acid | poor | Melting under decomposition at >160° C. | Not analyzed |
| Citric acid | high | melting under decomposition at >115° C. | Very hygroscopic (deliquescent) |
| Adipic acid | high | melting under decomposition at >169° C. | Not analyzed |
| Glycolic acid | high | 147° C. | Very hygroscopic (deliquescent) |
| p-Toluenesulfonic acid | moderate | melting under decomposition at >270° C. | Slightly hygroscopic |

[1)]Other salt formers (e.g., benzoic acid, succinic acid, glutaric acid, and acetic acid) were also tested, but did not readily lead to crystalline salts by following the herein described procedures.
[2)]The hygroscopicity of a compound is characterized (see, e.g., European Pharmacopoeia - 6th Edition (2008), Chapter 5.11) by the increase in mass when the relative humidity is raised from 0%-RH to 90%-RH at 25° C.:
non-hygroscopic: weight increase $\Delta m < 0.2\%$
slightly hygroscopic: weight increase $0.2\% \leq \Delta m < 2.0\%$
hygroscopic: weight increase $2.0\% \leq \Delta m < 15.0\%$
very hygroscopic: weight increase $\Delta m \leq 15.0\%$
deliquescent: sufficient water is adsorbed to form a liquid

Example 2: Recrystallization of Crude Salt Forms of 5-ethyl-4-methyl-N-[4-[(2S) morpholin-2-yl]phenyl]-1H-pyrazole-3-carboxamide The crude salts listed in Table 1 (except the salt with fumaric acid) were re-crystallized from appropriate solvent systems to improve the quality of the solids and to explore the tendency to form multiple crystal forms.

TABLE 2

Preparation, Crystallinities, Melting Temperatures, and Hygroscopicities of Re-Crystallized Salt Forms of 5-ethyl-4-methyl-N-[4-[(2S) morpholin-2-yl]phenyl]-1H-pyrazole-3-carboxamide.

| Salt former | Method for preparation | Crystallinity | Melting temperature (Tonset DSC) | Hygroscopicity[1)] |
|---|---|---|---|---|
| Hydrochloric acid | Approx. 300 mg of crude salt was dissolved in a mixture of 1.8 mL of ethanol and 0.6 mL of water at 75° C. The solution was then linearly cooled to 20° C. within 12 h without agitation. To increase the yield, the solvent was allowed to evaporate partially at ambient conditions. After filtration, the crystals were rinsed with ethanol, then dried in a vacuum tray dryer at 50° C./<10 mbar for 2 days. | high | >270° C. (melting under decomposition) | Non-hygroscopic (<0.1%-m/m weight increase) |
| Sulfuric acid | Approx. 350 mg of crude salt was dissolved in a mixture of 6.0 mL of ethanol and 4.4 mL of water at 75° C. The solution was then linearly cooled without agitation to 20° C. within 12 h and then from 20° C. to 10° C. within 6 h. After filtration, the crystals were rinsed with ethanol, followed by drying in a vacuum tray dryer at 50° C./<10 mbar for 2 days. | high | >260° C. (melting under decomposition) | Non-hygroscopic (0.1%-m/m weight increase) |
| Methanesulfonic acid | Approx. 350 mg of crude salt was dissolved in a mixture of 1.9 mL of ethanol and 1.0 mL of water at 75° C. After cooling without agitation, the solution was allowed to evaporate partially. Then, the solution was seeded with the crude salt to induce crystallization and further concentrated applying a gentle flow of nitrogen. After storage at 2-8° C. the solid lump was dissolved by adding 1 mL of ethanol. The solution was allowed to evaporate to dryness at ambient conditions. The hard solid residue was suspended in 2 mL of ethyl acetate. After filtration, the crystals were rinsed with ethyl acetate, followed by drying in a vacuum tray dryer at 50° C./<10 mbar for 2 days. | high | 218° C. | n.d. |
| Phosphoric acid | Approx. 350 mg of crude salt was dissolved in a mixture of 4.0 mL of ethanol and 3.5 mL of water at 75° C. The solution was then cooled without agitation and stored at 5° C. for approx. 2 weeks. To increase the yield, the solvent was allowed to evaporate partially at ambient | high | 230° C. (melting under decomposition) | Slightly hygroscopic (0.2%-m/m weight increase) |

TABLE 2-continued

Preparation, Crystallinities, Melting Temperatures, and Hygroscopicities of Re-Crystallized Salt Forms of 5-ethyl-4-methyl-N-[4-[(2S) morpholin-2-yl]phenyl]-1H-pyrazole-3-carboxamide.

| Salt former | Method for preparation | Crystallinity | Melting temperature (Tonset DSC) | Hygroscopicity[1)] |
|---|---|---|---|---|
| | conditions. After filtration, the crystals were rinsed with ethanol, followed by drying in a vacuum tray dryer at 50° C./<10 mbar for 2 days. | | | |
| L(+)-Tartaric acid | Approx. 400 mg of crude salt was dissolved in a mixture of 3.5 mL of ethanol and 1.0 mL of water at 75° C. The solution was then linearly cooled without agitation to 20° C. within 12 h and then from 20° C. to 10° C. within 6 h. For homogenization, the mixture was agitated at 5° C. overnight. After filtration, the crystals were rinsed with ethanol, followed by drying in avacuum tray dryer at 50° C./<10 mbar for 2 days. | high | Melting under decomposition at >170° C. | Slightly hygroscopic (0.4%-m/m weight increase) |
| Citric acid | Approx. 400 mg of crude salt was dissolved in a mixture of 2.0 mL of ethanol and 0.3 mL of water at 70° C. The solution was then linearly cooled without agitation to 5° C. within 12 h and then stored at 2-8° C. After approx, one week, the crystals were isolated by filtration and washed with ethanol, followed by drying 50° C./<10 mbar for 2 days. | high | 123° C. (melting under decomposition) | n.d. |
| Adipic acid | Approx. 300 mg of crude salt was dissolved in a mixture of 300 μL of ethanol and 30 μL of water at 65° C. The solution was then linearly cooled without agitation to 15° C. within 8 h and stored at 15° C. overnight. After filtration, the crystals were rinsed with ethanol, followed by drying in a vacuum tray dryer at 50° C./<10 mbar for 2 days. | high | 176° C. (melting under decomposition) | Slightly hygroscopic (0.2%-m/m weight increase) |
| Glycolic acid | Approx. 250 mg of crude salt was dissolved in a mixture of 1.0 mL of ethanol and 100 μL of water at 70° C. After cooling, the solution was allowed to evaporate passively at ambient conditions. The remaining oil was seeded with crude salt and then stored for approx, ten days at ambient temperature. The resulting solid residue was re-suspended in 1.0 mL of ethanol and stored in a refrigerator for three weeks. After filtration, the crystals were rinsed with ethanol, followed by | high | 148° C. | n.d. |

TABLE 2-continued

Preparation, Crystallinities, Melting Temperatures, and Hygroscopicities of Re-Crystallized Salt Forms of 5-ethyl-4-methyl-N-[4-[(2S) morpholin-2-yl]phenyl]-1H-pyrazole-3-carboxamide.

| Salt former | Method for preparation | Crystallinity | Melting temperature (Tonset DSC) | Hygroscopicity[1)] |
|---|---|---|---|---|
| | drying in a vacuum tray dryer at 50° C./<10 mbar for 2 days. | | | |
| p-Toluenesulfonic acid | Approx. 400 mg of crude salt was dissolved in a mixture of 5.0 mL of ethanol and 5.2 mL of water at 75° C. The solution was then linearly cooled without agitation to 20° C. within 12 h and then held at 20° C. overnight. The crystals were isolated by filtration and washed with ethanol, followed by drying 50° C./<10 mbar for 2 days. | high | 268° C. (melting under decomposition) | Non-hygroscopic (<0.1%-m/m weight increase) |

[1)]See definition in Table 1 above

Example 3: Preparation of Crystalline Form A of 5-ethyl-4-methyl-N-[4-[(2S) morpholin-2-yl]phenyl]-1H-pyrazole-3-carboxamide, mono hydrochloric acid salt 5-ethyl-4-methyl-N-[4-[(2S) morpholin-2-yl]phenyl]-1H-pyrazole-3-carboxamide (20.02 g, 63.68 mmol) was dissolved in a mixture of 1-propanol and water at 85° C. (252 g of solvent mixture, 8%-m/m water). Aqueous HCl solution was added (25%, 8.48 mL, 1.03 equivalents). Supersaturation was generated by a first cooling step to 60° C. Seeding was performed with milled mono hydrochloride salt of 5-ethyl-4-methyl-N-[4-[(2S) morpholin-2-yl]phenyl]-1H-pyrazole-3-carboxamide, mono hydrochloric acid salt crystals (crystal Form A). The water content was then reduced to less than 2% by distillation. During this operation, the volume in the reactor was kept constant by adding fresh 1-propanol. After distillation, the suspension was cooled to the isolation temperature of 0° C., followed by final ageing and filtration. The wet cake was washed with 1-propanol and dried under vacuum (60° C./25 mbar for 16 h), yielding colorless crystals (21.81 g, 95% yield) of the mono hydrochloride salt of 5-ethyl-4-methyl-N-[4-[(2S) morpholin-2-yl]phenyl]-1H-pyrazole-3-carboxamide.

Example 4: Preparation of Crystalline Form A of 5-ethyl-4-methyl-N-[4-[(2S) morpholin-2-yl]phenyl]-1H-pyrazole-3-carboxamide, hemi sulfuric acid salt 5-ethyl-4-methyl-N-[4-[(2S) morpholin-2-yl]phenyl]-1H-pyrazole-3-carboxamide (700 mg, 2.23 mmol) was suspended in ethanol (100 mL) in a closed glass vessel at ambient temperature using magnetic agitation. Sulfuric acid (96%, 68 1.22 mmol, 0.55 equivalents) was added dropwise. The resulting rich suspension was agitated for 2 days at ambient temperature. The product was then isolated by filtration using a filter nutsche with a paper filter. The residue was rinsed with ethanol (5 mL) and then dried in a vacuum tray dryer at 50° C./<10 mbar for two days yielding a colorless solid (690 mg, 85% yield) of the hemi sulfuric acid salt of 5-ethyl-4-methyl-N-[4-[(2S) morpholin-2-yl]phenyl]-1H-pyrazole-3-carboxamide.

Melting temperature: >260° (melting under decomposition)

DVS: n.d.

Example 5: Preparation of Crystalline Form A of 5-ethyl-4-methyl-N-[4-[(2S) morpholin-2-yl]phenyl]-1H-pyrazole-3-carboxamide, mono phosphoric acid salt 5-ethyl-4-methyl-N-[4-[(2S) morpholin-2-yl]phenyl]-1H-pyrazole-3-carboxamide (700 mg, 2.23 mmol) was suspended in ethanol (100 mL) in a closed glass vessel at ambient temperature using magnetic agitation. Phosphoric acid (85%, 165 2.45 mmol, 1.10 equivalents) was added. The resulting rich suspension was agitated for 2 days at ambient temperature. The product was then isolated by filtration using a filter nutsche with a paper filter. The residue was rinsed with ethanol (5 mL) and then dried in a vacuum tray dryer at 50° C./<10 mbar for two days yielding a colorless solid (870 mg, 95% yield) of the mono phosphoric acid salt of 5-ethyl-4-methyl-N-[4-[(2S) morpholin-2-yl]phenyl]-1H-pyrazole-3-carboxamide.

Melting temperature: >230° (melting under decomposition)

DVS: n.d.

Example 6: Preparation of Crystalline Form A of 5-ethyl-4-methyl-N-[4-[(2S) morpholin-2-yl]phenyl]-1H-pyrazole-3-carboxamide, mono p-toluenesulfonic acid salt 5-ethyl-4-methyl-N-[4-[(2S) morpholin-2-yl]phenyl]-1H-pyrazole-3-carboxamide (700 mg, 2.23 mmol) was suspended in ethanol (100 mL) in a closed glass vessel at ambient temperature using magnetic agitation. p-Toluenesulfonic acid (99.0%, 426 mg, 2.45 mmol, 1.10 equivalents) was added. The resulting rich suspension was agitated for 3 days at ambient temperature. The product was isolated by filtration using a filter nutsche with a paper filter. The residue was rinsed with ethanol (5 mL) and then dried in a vacuum tray dryer at 50° C./<10 mbar for two days yielding a colorless solid (988 mg, 91% yield) of the mono p-toluenesulfonic acid salt of 5-ethyl-4-methyl-N-[4-[(2S) morpholin-2-yl]phenyl]-1H-pyrazole-3-carboxamide.

Melting temperature: 272° C. (melting under decomposition)

DVS: n.d.

Example 7: X-Ray Powder Diffraction (XRPD)

Experimental Methodology

X-ray diffraction patterns were recorded at ambient conditions in transmission geometry with a STOE STADI P diffractometer (Cu Kα radiation (1.5406 Å), primary Ge-monochromator, Mythen 1K silicon strip detector, angular range 3° to 42° 2Theta, 20 seconds measurement time per step). The samples were prepared and analysed without further processing (e.g. grinding or sieving) of the substance.

Measurement and evaluation of the X-ray diffraction data was done using WinXPOW software (STOE & Cie GmbH, Darmstadt, Germany).

Results

Form A of each of the mono hydrochloric acid salt, the hemi sulfuric acid salt, the mono phosphoric acid salt and the mono p-toluenesulfonic acid salt of 5-ethyl-4-methyl-N-[4-[(2S) morpholin-2-yl]phenyl]-1H-pyrazole-3-carboxamide were characterized by XRPD. The unique peaks of the different crystalline salts are presented in Table 3. Characteristic XRPD diffractograms for the individual salts are shown in FIG. 1 and FIG. 4 to FIG. 6.

TABLE 3

XRPD peaks typical for Form A of the four different salts

| Mono HCl salt | | Hemi sulfuric acid salt | | Mono phosphoric acid salt | | Mono p-toluenesulfonic acid salt | |
|---|---|---|---|---|---|---|---|
| Unique peaks [°2Theta] | rel. Intensity [%] | Unique peaks [°2Theta] | rel. Intensity [%] | Unique peaks [°2Theta] | rel. Intensity [%] | Unique peaks [°2Theta] | rel. Intensity [%] |
| 3.4 | 30 | 3.4 | 89 | 3.4 | 100 | 6.6 | 19 |
| 6.7 | 45 | 6.8 | 10 | 10.3 | 18 | 7.1 | 3 |
| 10.1 | 19 | 7.2 | 8 | 12.4 | 3 | 13.1 | 9 |
| 13.5 | 13 | 7.7 | 4 | 13.9 | 7 | 16.1 | 31 |
| 15.4 | 100 | 8.2 | 4 | 14.8 | 18 | 16.3 | 18 |
| 15.6 | 79 | 9.5 | 5 | 14.9 | 21 | 16.9 | 4 |
| 15.8 | 81 | 10.2 | 26 | 15.8 | 6 | 18.3 | 21 |
| 16.6 | 47 | 13.6 | 9 | 15.9 | 6 | 19.0 | 100 |
| 16.9 | 9 | 14.5 | 34 | 17.0 | 8 | 19.7 | 7 |
| 18.0 | 63 | 14.8 | 6 | 17.3 | 21 | 20.5 | 9 |
| 19.0 | 27 | 15.1 | 4 | 17.5 | 4 | 21.5 | 2 |
| 20.3 | 12 | 15.4 | 20 | 18.4 | 11 | 22.1 | 11 |
| 20.8 | 22 | 15.8 | 8 | 18.9 | 3 | 22.4 | 6 |
| 21.1 | 10 | 16.5 | 7 | 19.3 | 14 | 23.4 | 16 |
| 22.1 | 15 | 16.9 | 49 | 21.1 | 26 | 23.9 | 4 |
| 22.6 | 5 | 17.3 | 11 | 21.3 | 14 | 24.4 | 2 |
| 23.1 | 95 | 17.4 | 10 | 21.5 | 60 | 24.7 | 27 |
| 23.2 | 58 | 17.8 | 7 | 21.8 | 10 | 25.8 | 2 |
| 23.8 | 8 | 18.2 | 25 | 22.3 | 6 | 26.6 | 2 |
| 25.0 | 85 | 19.0 | 7 | 23.0 | 3 | 27.6 | 6 |
| 25.2 | 50 | 19.5 | 15 | 23.7 | 8 | 28.4 | 2 |
| 25.9 | 33 | 19.7 | 5 | 23.8 | 4 | 28.7 | 3 |
| 27.0 | 9 | 21.3 | 100 | 24.1 | 2 | 28.9 | 4 |
| 27.9 | 17 | 21.7 | 13 | 24.4 | 2 | 29.6 | 3 |
| 28.1 | 7 | 21.9 | 24 | 25.5 | 4 | 29.8 | 7 |
| 30.3 | 17 | 22.2 | 14 | 25.8 | 18 | 30.3 | 2 |
| 30.6 | 28 | 22.5 | 11 | 26.4 | 7 | 30.4 | 5 |
| 31.0 | 10 | 22.7 | 9 | 26.7 | 4 | 32.0 | 3 |
| 31.3 | 6 | 23.5 | 30 | 27.3 | 16 | 32.5 | 5 |
| 31.6 | 27 | 23.9 | 10 | 27.9 | 3 | 33.4 | 3 |
| 32.5 | 11 | 24.5 | 5 | 28.4 | 6 | 34.4 | 2 |
| 33.5 | 8 | 25.1 | 31 | 28.5 | 3 | 35.2 | 2 |
| 33.6 | 9 | 25.6 | 5 | 29.1 | 11 | 36.3 | 3 |
| | | 26.0 | 14 | 29.8 | 3 | | |
| | | 27.1 | 16 | 30.4 | 6 | | |
| | | 27.2 | 4 | | | | |
| | | 27.7 | 6 | | | | |
| | | 28.7 | 9 | | | | |
| | | 29.3 | 11 | | | | |
| | | 30.0 | 5 | | | | |
| | | 31.8 | 6 | | | | |
| | | 32.0 | 9 | | | | |

Example 8: Differential Scanning Calorimetry (DSC) and Thermogravimetric Analysis (TGA)

The DSC-thermograms were recorded using a Mettler-Toledo differential scanning calorimeter DSC1/2, DSC820/821e or a TA Instruments Discovery Series. For the measurements, approximately 2 to 6 mg of sample were placed in aluminum pans, accurately weighed and hermetically closed with perforation lids. Prior to measurement, the perforation lids were pierced resulting in approx. 0.5 mm pin holes. In order to measure the sample under pressure, closed lids can also be used. The samples were then heated under a flow of nitrogen of about 100 mL/min applying a heating rate of typically 1 to 20, usually 10 K/min to a maximum temperature of typically 180° C.-350° C. (depending on decomposition temperature).

Thermogravimetric analyses (TGA) were performed on a Mettler-Toledo thermogravimetric analyzer TGA/DSC1, TGA/DSC3+or TGA851e/SDTA. For the thermogravimetric analyses, approximately 5 to 15 mg of sample were placed in aluminum pans, accurately weighed, and hermetically closed with perforation lids. Prior to measurement, the lids were automatically pierced resulting in approx. 0.5 mm pin holes. The samples were then heated under a flow of nitrogen of about 50 mL/min applying a heating rate of 5 K/min up to a maximum temperature of typically 350° C.

Crystalline Form A of 5-ethyl-4-methyl-N-[4-[(2S) morpholin-2-yl]phenyl]-1H-pyrazole-3-carboxamide, hydrochloric acid salt A sample of Form A of 5-ethyl-4-methyl-N-[4-[(2S) morpholin-2-yl]phenyl]-1H-pyrazole-3-carboxamide, hydrochloric acid salt was analyzed by DSC and TGA. DSC analysis of Form A showed an endotherm having an onset at about 270° C. (melt and decomposition overlapping). TGA analysis showed continuous weight loss at <260° C. indicating beginning decomposition.

Example 9: Dynamic Vapour Sorption (DVS)

Moisture sorption/desorption data were collected on a DVS Advantage, a DVS Adventure, or a DVS Intrinsic (SMS Surface Measurements Systems) moisture balance system. The sorption/desorption isotherms were measured stepwise in a range from 0%-RH to 90%-RH at typically 25° C. A weight change of typically <0.001%/min was chosen as criterion to switch to the next level of relative humidity (with a maximum equilibration time of typically 24 hours, if the weight change criterion was not met). The data were corrected for the initial moisture content of the samples by taking the weight after drying of the samples at 0%-RH as zero point. The hygroscopicity of a given substance is characterized (by close analogy with the European Pharmacopoeia) by the increase in mass when the relative humidity is raised from 0%-RH to 90%-RH at 25° C.:

| | | |
|---|---|---|
| non-hygroscopic: | weight increase | $\Delta m < 0.2\%$ |
| slightly hygroscopic: | weight increase | $0.2\% \leq \Delta m < 2.0\%$ |
| hygroscopic: | weight increase | $2.0\% \leq \Delta m < 15.0\%$ |
| very hygroscopic: | weight increase | $\Delta m \geq 15.0\%$ |
| deliquescent: | sufficient water is adsorbed to form a liquid | |

Crystalline Form A of 5-ethyl-4-methyl-N-[4-[(2S) morpholin-2-yl]phenyl]-1H-pyrazole-3-carboxamide, hydrochloric acid salt The DVS analysis of Form A of 5-ethyl-4-methyl-N-[4-[(2S) morpholin-2-yl]phenyl]-1H-pyrazole-3-carboxamide, hydrochloric acid salt showed <0.1% mass uptake between 0-90% RH with no hysteresis and rate of water uptake was observed to increase at >80% RH.

Example 10: Aqueous Solubility

Aqueous solubility was determined by suspending sufficient compound in water water to give a maximum final concentration of 100 mg/mL. The solution was stirred for 24 hours at room temperature (25° C.±5° C.) on a magnetic stirrer using a magnetic stir bar. The final pH of the suspension was measured after 24 hours with a standard pH meter. The suspension was filtered by centrifugation through a ≤0.45 μm PVDF filter. The filtrate was then diluted 1:500 using a solution of ethanol: water (1:1). Quantification was by HPLC using a previously developed HPLC method (Table 4). A standard curve with a concentration range from 0.001 mg/mL-0.3 mg/ml. The solubility was automatically calculated using the peak area of the main peak in the chromatogram.

Aqueous solubility was determined by suspending sufficient compound in water to give a maximum final concentration of ≥10 mg/mL of the parent free-form of the compound. The suspension was equilibrated at 25° C. for 24 hours then the pH was measured. The suspension was then filtered through a glass fibre C filter. The filtrate was then diluted by an appropriate factor e.g. 101. Quantitation was by HPLC with reference to a standard solution of approximately 0.25 mg/mL in DMSO. Different volumes of the standard, diluted and undiluted sample solutions were injected. The solubility was calculated using the peak areas determined by integration of the peak found at the same retention time as the principal peak in the standard injection.

TABLE 4

HPLC Method Parameters for Solubility Measurements

| | | | |
|---|---|---|---|
| Type of method: | Reverse phase with gradient elution | | |
| Column: | Column Waters, Acquity UPLC BEH C18 1.7 um, 2.1 × 50 mm | | |
| Column Temperature (° C.): | 30 | | |
| Test Injection (μl): | 1 | | |
| Detection: Wavelength, Bandwidth (nm): | 266 | | |
| Flow Rate (mL/min): | 0.5 | | |
| Phase A: | 0.01M Phosphoric acid in water | | |
| Phase B: | 0.01M Phosphoric acid in acetonitrile | | |
| Timetable: | Time (min) | % Phase A | % Phase B |
| | 0.0 | 90 | 10 |
| | 0.1 | 90 | 10 |
| | 1.8 | 5 | 95 |
| | 1.9 | 5 | 95 |
| | 1.95 | 80 | 20 |
| | 2.0 | 90 | 10 |

Analysis was performed on a UPLC Aquity Waters system equipped with a diode array detector Type UPLC LG 500 nm and using Empower3 software.

A saturated aqueous solution of crystalline Form A of 5-ethyl-4-methyl-N-[4-[(2S) morpholin-2-yl]phenyl]-1H-pyrazole-3-carboxamide, hydrochloric acid salt was observed to have an aqueous solubility of 52.8 mg/mL with a pH of 5.3.

The invention claimed is:

1. A pharmaceutically acceptable salt of 5-ethyl-4-methyl-N-[4-[(2S) morpholin-2-yl]phenyl]-1H-pyrazole-3-carboxamide (Formula I)

(I)

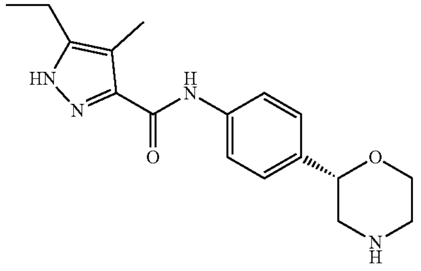

wherein the pharmaceutically acceptable salt is a mono hydrochloric acid salt and wherein the salt is in crystalline form.

2. The crystalline mono hydrochloric acid salt according to claim 1, wherein said crystalline mono hydrochloric acid salt has an X-ray powder diffraction (XRPD) pattern with characteristic peaks at 3.4, 6.7, 10.1, 13.5, 15.4, 15.6, 15.8, 16.6, 18.0, 23.1, 23.2, 25.0, and 25.9 [° 2 Theta±0.2° 2 Theta, Cu Kα radiation (1.5406 Å)].

3. The crystalline mono hydrochloric acid salt according to claim 1, wherein said crystalline mono hydrochloric acid salt has an X-ray powder diffraction (XRPD) pattern with characteristic peaks at 3.4, 6.7, 10.1, 13.5, 15.4, 15.6, 15.8, 16.6, 18.0, 19.0, 20.3, 20.8, 21.1, 22.1, 23.1, 23.2, 25.0, 25.2, and 25.9 [° 2 Theta±0.2° 2 Theta, Cu Kα radiation (1.5406 Å)].

4. The crystalline mono hydrochloric acid salt according to claim 1, wherein said crystalline mono hydrochloric acid salt has an X-Ray powder diffraction (XRPD) pattern as shown in FIG. 1.

5. A process for manufacturing the crystalline mono hydrochloric acid salt according to claim 1, comprising:

(a) reacting 5-ethyl-4-methyl-N-[4-[(2S) morpholin-2-yl] phenyl]-1H-pyrazole-3-carboxamide with hydrochloric acid; and (b) adding seed crystals of 5-ethyl-4-methyl-N-[4-[(2S) morpholin-2-yl]phenyl]-1H-pyrazole-3-carboxamide, mono hydrochloric acid salt to the mixture obtained from step (a).

6. The process of claim 5, wherein steps (a) and (b) are performed in a solvent mixture of an alcohol and water.

7. The process of claim 6, wherein said alcohol is 1-propanol.

8. The process of claim 6, wherein the ratio of alcohol to water in step (a) is 15:1 vol/vol.

9. The process according to claim 5, wherein the hydrochloric acid is added as an aqueous solution.

10. The process according to claim 9, wherein said aqueous solution of hydrochloric acid comprises 25% wt/wt of hydrochloric acid.

11. The process according to claim 5, further comprising step (c): reducing the water content of the reaction mixture by distillation.

12. The process according to claim 11, wherein the water content after said reducing the water content of the reaction mixture is 2% wt/wt.

13. The process according to claim 5, further comprising step (d): cooling.

14. The process according to claim 13, wherein said cooling is cooling to 0° C.+/−5° C.

15. The process according to claim 5, further comprising step (e): ageing.

16. The process according to claim 15, wherein said ageing is ageing at 0° C.+/−5° C.

17. The process according to claim 15, wherein said ageing is for at least 4 h.

18. The process according to claim 5, wherein said seed crystals are added as a suspension in an organic solvent.

19. The process according to claim 18, wherein said organic solvent is 1-propanol.

20. A pharmaceutically acceptable salt of 5-ethyl-4-methyl-N-[4-[(2S) morpholin-2-yl]phenyl]-1H-pyrazole-3-carboxamide (Formula I)

(I)

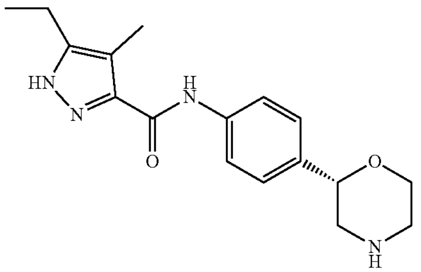

wherein the pharmaceutically acceptable salt is a mono hydrochloric acid salt and wherein the salt is in the crystalline form obtained by the process according to claim 5.

21. A pharmaceutical composition comprising an effective amount of the crystalline mono hydrochloric acid salt according to claim 1, and at least one additional ingredient selected from pharmaceutically acceptable carriers, diluents and excipients.

22. The pharmaceutical composition according to claim 21, wherein the pharmaceutical composition is in a form suitable for oral administration to a mammal.

23. The pharmaceutical composition according to claim 22, wherein the oral pharmaceutical composition is a solid dosage form.

24. The pharmaceutical composition according to claim 22, wherein the oral pharmaceutical composition is selected from the group consisting of tablets, coated tablets, dragées, hard gelatin capsules, soft gelatin capsules, solutions, suspensions and emulsions.

25. The pharmaceutical composition according to claim 21, wherein the pharmaceutical composition comprises 20 mg to 400 mg of said crystalline 5-ethyl-4-methyl-N-[4-[(2S) morpholin-2-yl]phenyl]-1H-pyrazole-3-carboxamide, mono hydrochloric acid salt.

26. A method of treating schizophrenia in a mammal comprising administering to the mammal an effective amount of the crystalline mono hydrochloric acid salt of claim 1 or a pharmaceutical composition comprising an effective amount of the crystalline mono hydrochloric acid salt of claim 1 and at least one additional ingredient selected from pharmaceutically acceptable carriers, diluents and excipients.

* * * * *